(12) United States Patent
Greff (10) Patent No.: US 9,403,028 B2
(45) Date of Patent: Aug. 2, 2016

(54) DEVICE FOR EMITTING A MAGNETIC FIELD

(75) Inventor: Daniel Greff, Mere (FR)

(73) Assignee: COSMOSOFT, Levallois-Perret (FR)

( * ) Notice: Subject to any disclaimer, the term of this patent is extended or adjusted under 35 U.S.C. 154(b) by 270 days.

(21) Appl. No.: 13/980,812

(22) PCT Filed: Jan. 20, 2012

(86) PCT No.: PCT/FR2012/050127
§ 371 (c)(1),
(2), (4) Date: Aug. 22, 2013

(87) PCT Pub. No.: WO2012/098338
PCT Pub. Date: Jul. 26, 2012

(65) Prior Publication Data
US 2013/0331637 A1 Dec. 12, 2013

(30) Foreign Application Priority Data

Jan. 21, 2011 (FR) .................................. 11 50494
Jan. 21, 2011 (FR) .................................. 11 50496

(51) Int. Cl.
*A61N 1/00* (2006.01)
*A61N 2/00* (2006.01)
*A61N 1/40* (2006.01)
*A61N 2/02* (2006.01)

(52) U.S. Cl.
CPC .. *A61N 2/00* (2013.01); *A61N 1/40* (2013.01); *A61N 2/02* (2013.01)

(58) Field of Classification Search
CPC ........... A61N 2/00; A61N 2/004; A61N 2/02; A61N 2/12
USPC ....................................................... 600/9–15
See application file for complete search history.

(56) References Cited

U.S. PATENT DOCUMENTS

| | | |
|---|---|---|
| 4,266,532 A | 5/1981 | Ryaby et al. |
| 4,850,959 A | 7/1989 | Findl |
| 5,100,373 A | 3/1992 | Liboff et al. |
| 5,620,463 A | 4/1997 | Drolet |
| 6,261,221 B1 | 7/2001 | Tepper et al. |
| 2003/0045770 A1 | 3/2003 | Van Mullekom |
| 2004/0193003 A1 | 9/2004 | Mechlenburg et al. |
| 2005/0228210 A1 | 10/2005 | Muntermann |
| 2006/0235491 A1 | 10/2006 | Piotrowicz |
| 2008/0139871 A1 | 6/2008 | Muntermann |

OTHER PUBLICATIONS

International Search Report, International Application No. PCT/FR2012/050127, dated Mar. 4, 2012.

*Primary Examiner* — John Lacyk
(74) *Attorney, Agent, or Firm* — Dawn C. Russell; Culhane Meadows PLLC (57) ABSTRACT

The invention relates to a device that can be used to expose a person to a magnetic field, including an insulating belt to be placed in contact with a part of the body of the person, at least one substantially rectangular, flat dipole antenna emitting a magnetic field over a vector perpendicular to the surface thereof, the antenna being arranged longitudinally on the belt in the lengthwise direction thereof, and a power source for supplying the antenna with AC or pulsed power.

45 Claims, 3 Drawing Sheets

DEVICE FOR EMITTING A MAGNETIC FIELD

CROSS REFERENCED TO RELATED APPLICATIONS

This application is a National Stage entry of International Application PCT/FR2012/050127 filed Jan. 20, 2012, which claims priority to French Application Nos. 1150494 and 1150496, both filed Jan. 21, 2011, the disclosure of these prior applications are hereby incorporated in their entirety by reference.

BACKGROUND OF THE INVENTION

The present invention relates to the general field of the use of electromagnetic waves to act on the metabolism of the human body in order to induce physiological changes, in particular to promote sleep, increase fertility, and treat adipose overloads.

An electromagnetic field is the composition of two vector fields that can be measured independently: an electrical field and a magnetic field. The component of the electrical field, present throughout the electromagnetic field, becomes significant from a frequency of 1 KHz, whereas, at a frequency of 50 Hz for example, the magnetic field predominates. In this application, the term magnetic field will be used to describe an electromagnetic field in which the magnetic component is predominant.

The application of a low frequency or high frequency electromagnetic field to reduce the adipose mass has been suggested many times in the prior art. However, no effective method against obesity has hitherto been found.

Reducing fatty mass by the application of a magnetic field has already been proposed. Reference can in particular be made to the documents FR 2,855,415, FR 2,906,727 and EP 2,068,810.

These documents describe devices for treating adipose overloads consisting of insulating straps applied to the part of the human body to be treated (abdomen, arm, thigh or calf), these straps being equipped with a conductor folded in successive strands and linked to an electromagnetic wave generator. In the document EP 2,068,810, the device also comprises a pressure therapy apparatus overlaid on the straps.

Although exhibiting certain results on the reduction of bodily fatty mass, the effectiveness of these devices remains limited. This is because these devices stimulate lipolysis only in the surface tissues.

Other treatment methods applied to the human body which apply low frequency electromagnetic fields have been described.

The document US 2010/0130945 in particular proposes preventing myocardial infarctions by applying a magnetic field whose intensity is varied according to the area of the body to which it is applied. The magnetic field would act on the muscular cells of the arteries or on the myocytes of the myocardium to relax the muscles and enhance blood perfusion.

The document US 2007/0255085 teaches the stimulation of the nerve tissues of a patient by combining ultrasounds with two magnetic fields, primarily in order to attenuate the pain. The document U.S. Pat. No. 5,100,373 proposed treating osteoporosis by applying a magnetic field with a frequency equal to 16 Hz and an amplitude equal to 20.9 or 12.7 microT.

Finally, the document WO 2008/127011 describes the complete irradiation of the body by a magnetic field with an intensity of between 3 and 30 microT, to act on the bipolarization of the cellular membranes and stimulate in particular the neurons, the muscular cells and the walls of the blood vessels. This document suggests applying this method to treat a large number of diseases, including obesity. The frequency of the magnetic field applied is chosen to be equal to the resonant frequency of water molecules (12.5 Hz, 16.3 Hz, 23.4 Hz, 39.6 Hz, 87 Hz or 250 Hz) or to one of the frequencies of the brainwaves conditioning growth, concentration or memory for example.

The application of a high frequency electromagnetic field to reduce adipose mass has also been proposed.

The US patent application 2009/0125013 in particular describes a method for reducing adipose tissues by the application of electromagnetic waves of very high frequency, between 1 and 50 MHz. According to this method, the frequency and the polarity of an electrical field are adapted to the impedance of the adipose cells to destroy the lipid globules that are found inside the cells or to destroy the cellular membrane of the adipocytes. The form of the electrical field is generated by the association of two antennas respectively emitting in the plane parallel to the skin and in the perpendicular plane so as to be able to adapt the polarity of the electrical field to the form of the adipose area of the body to be treated.

Methods for treating various diseases by thermotherapy have also been proposed in the patent application US 2005/0090732. According to this method, the heat generated by an electromagnetic field with a frequency of between 0.1 and 900 MHz would theoretically make it possible to target the diseased cells by raising their temperature between 40 and 46° C., in order to destroy them. An entire list of diseases, including cancer, Aids, restenosis, tuberculosis and obesity, is given. This method has not however been proven in the treatment of obesity.

A device comprising a series of flat coplanar coils which overlap and which are supplied individually by a pulsed current has already been proposed in the application US 2003/0158583 to stimulate the nerves or contract the muscles and treat various biological disorders by a high frequency electromagnetic field in which the electrical component is predominant. However, this device is designed to generate a diffuse electrical field which is always directed toward the center of the body, so that it does not make it possible to target a particular area of the body. Furthermore, this device has the drawback of lacking safety in use, because the coils can easily slip relative to one another, and the current voltages used to operate it are very high.

The document WO 1996/16692 also describes a device in coil form for generating an electromagnetic field of very high frequency, typically between 20 and 50 kHz, and of very high intensity, of the order of 2 Tesla, for contracting the abdominal muscles or stimulating the nerves. This device offers risks to health because it exposes the organs of the body such as the heart, the lungs or the brain to excessively intense electromagnetic waves.

OBJECT AND SUMMARY OF THE INVENTION

The main aim of the present invention is therefore to mitigate such drawbacks by proposing a device that is particularly effective in its action on the body, in particular for reducing adipose overloads, and inoffensive to the health of the person exposed.

This aim is achieved by virtue of a device for exposing at least a part of the body of a person to a magnetic field comprising, in accordance with the invention, an insulating belt intended to be applied in contact with a part of the body of a person, at least one substantially rectangular flat dipolar antenna emitting a magnetic field on a vector perpendicular to its surface, the antenna being positioned longitudinally on the belt in the lengthwise direction thereof, and an alternating or pulsed current power supply source for the antenna.

The antenna or antennas of the device according to the invention emit a magnetic field directed locally toward certain areas of the body to be treated, namely, in particular, the abdominal belt, the arms, the thighs, the calfs and the back. The application of this magnetic field makes it possible to simulate a sporting activity, in particular by its action on the calcium channels, and does so without any muscular contraction felt by the patient. Also, it has been discovered that this device makes it possible not only to reduce the visceral or intramuscular fatty mass, but also to fight against obesity, to fight against metabolic syndrome, and to very significantly increase the chances of medically-assisted procreation in sterile people.

Moreover, the device according to the invention offers the particular feature that the magnetic field is emitted by flat and rectangular dipolar antennas which are positioned longitudinally in the lengthwise direction of the belt. Also, when the device is, for example, applied to the abdominal belt, the main component of this magnetic field is not coaxial to the vertebral column of the person and is very weak when the field reaches the critical areas of the body (heart, lung, brain). This means that the use of the device according to the invention offers little risk to the health of the person.

The alternating or pulsed power supply current for the antenna can have a frequency of between 10 and 100 Hz, preferably between 40 and 60 Hz. It can be equal to 16 Hz, 32 Hz, 48 Hz, 64 Hz, 80 Hz or 96 Hz, preferably of the order of 50 Hz. "Alternating current" should be understood to mean that the value and the direction of the instantaneous current change. "Pulsed current" should be understood to mean that only the value of the instantaneous current changes, its direction (negative or positive) always remaining the same. Although possible, the use of a pulsed current nevertheless offers less impressive results than with the use of an alternating power supply current.

Furthermore, when the power supply current of the antenna is an alternating current, it preferably has a voltage of the order of 5 to 25 V, for example approximately 10 or 20 V, and an intensity of between 0.3 and 0.8 A, for example of the order of 0.5 A. It has indeed been found that a power supply current exhibiting such characteristics makes it possible to obtain the best results in terms of emitted magnetic field density and of energy density avoiding placing the patient in a situation of electrical or thermal risks.

The voltage of the power supply current for the device is preferably between 5 and 25 V, preferably between 5 and 15 V. It can also be equal to 20 V in certain embodiments. The intensity of the power supply current for the device is preferably between 0.3 and 0.8 A, also preferably between 0.5 and 0.8 A, more preferentially equal to 0.5 A.

Advantageously, the antenna is dimensioned to emit a magnetic field with a maximum intensity of approximately 200 microTesla (200 µT). It has indeed been found that the application of a magnetic field of intensity greater than 200 µT (or 2 Gauss) can have, at high doses, damaging secondary effects on the cells of the brain and of the bones of the person. The limitation to such an intensity threshold of 200 µT therefore makes it possible to avoid such risks.

According to one embodiment, the belt is an abdominal belt having two parallel rows of flat dipolar antennas, each row consisting of a central antenna positioned between two lateral antennas, the antennas of one and the same row being supplied in series.

In this case, the antennas of one and the same row are preferably supplied with alternating current in such a way that the central antenna emits a magnetic field on a vector opposite in direction to the vector on which the magnetic field emitted by the lateral antennas is emitted.

According to another embodiment, the belt is a belt intended to be worn around the arm or the calf of a person, said belt having a single flat dipolar antenna.

According to yet another embodiment, the belt is a belt intended to be worn around the thigh of a person, said belt having two parallel rows of flat dipolar antennas, each row consisting of two lateral antennas supplied in series.

According to another embodiment, the belt is in the form of a mat on which the person lies down. The mat can be placed on the mattress of a bed. It can also serve as a relaxation or gymnastic mat. When the belt takes the form of a mat, at least two antennas, preferably at least four, also preferably at least six, are advantageously used, positioned parallel in their lengthwise direction. The mat will preferably be placed in such a way that the antennas are situated in immediate proximity to the back, also preferably to the bottom of the back toward the middle of the back.

The device of the invention may also comprise a module for controlling the alternating current power supply source for the antenna and at least one magnetic field measurement sensor positioned on the belt and linked to said control module. The presence of one or more magnetic field measurement sensors makes it possible to accurately determine the threshold of magnetic induction applied to the person. Based on these measurements, an adjustment can therefore be made using the control module.

BRIEF DESCRIPTION OF THE DRAWINGS

Other features and advantages of the present invention will become apparent from the description given below, with reference to the attached drawings which illustrate exemplary embodiments thereof but which are in no way limiting. In the figures.

DETAILED DESCRIPTION OF EMBODIMENTS

Figure 1:
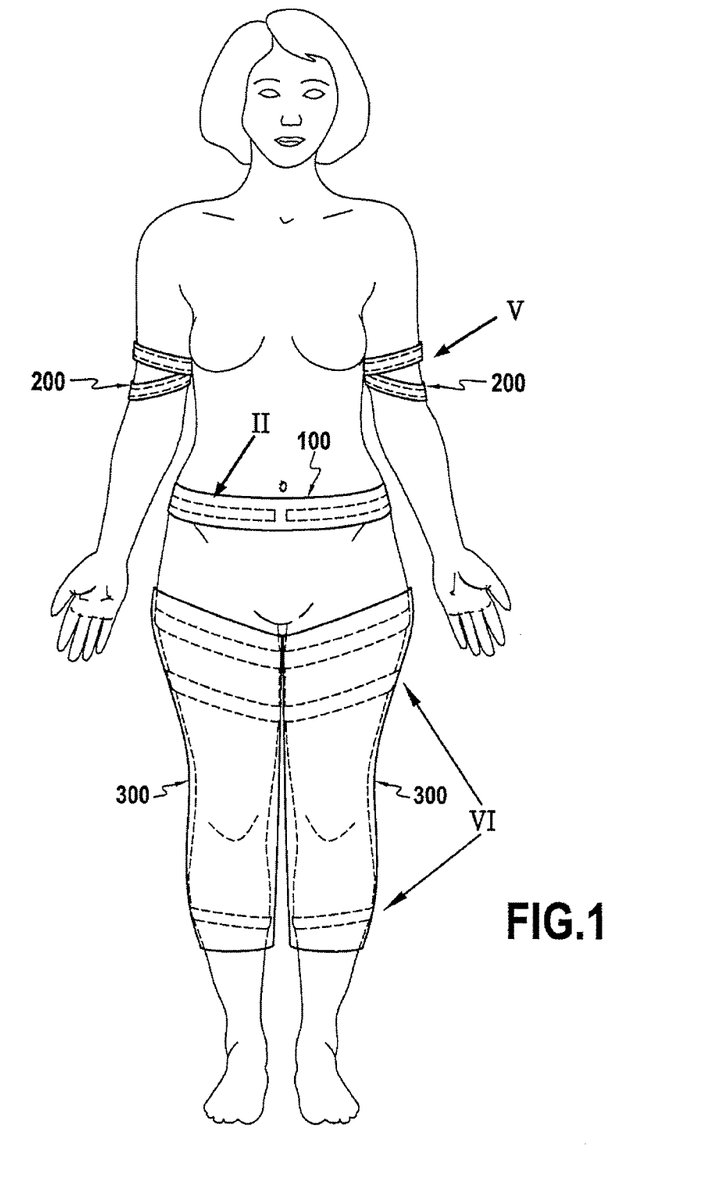
FIG. 1 is a view of a person provided with devices according to different embodiments of the invention.

The device according to the invention can be applied to different parts of the body of a person. FIG. 1 thus illustrates a plurality of devices, namely: a device 100 positioned around the abdominal belt of a person, devices 200 positioned around the arms of the person, and devices 300 positioned around the thigh and the calf of each leg of the person.

The device can also be placed on the back of a person, preferably between the bottom and the middle of the back.

The aim of these devices 100 to 300 is to emit to these parts of the body of the person magnetic fields whose characteristics (of direction and of intensity in particular) aim to reduce the fatty mass present in these parts. This reduction of the adipose overloads is made possible by virtue of the effect of the magnetic field generated by the device according to the invention which simulates a sporting activity.

Whatever the part of the body to which it is applied, the device according to the invention comprises an insulating belt, at least one substantially rectangular flat dipolar antenna emitting a magnetic field on a vector perpendicular to its surface, the antenna being positioned longitudinally on the belt in the lengthwise direction thereof, and an alternating current power supply source for the antenna.

Figure 2:
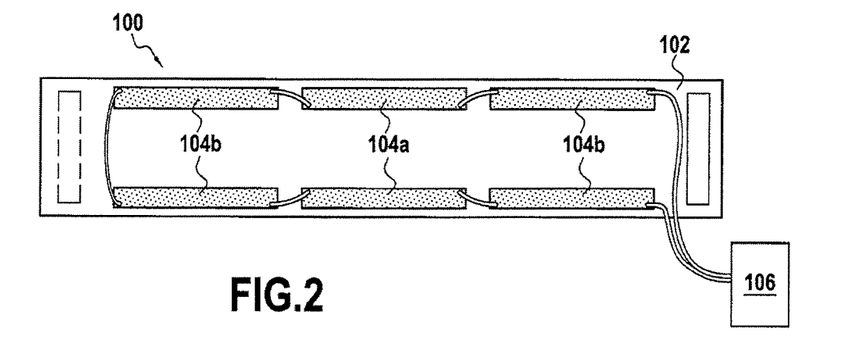
FIG. 2 is a view of the device of FIG. 1 in the form of an abdominal belt.

Thus, as represented in FIG. 2, the device 100 intended to be applied around the abdominal belt comprises a belt 102 made of an insulating material, for example of PVC-coated polyester, and it can be closed in the manner of a clothing belt.

The belt 102 comprises two parallel rows of flat dipolar antennas, each row of antennas consisting of a central antenna 104a positioned between two lateral antennas 104b. The antennas are more specifically substantially rectangular and positioned in the lengthwise direction of the belt 102 (they extend longitudinally in the lengthwise direction of the belt as represented in FIG. 2). Moreover, they can, for example, be positioned between two sheets of insulating material constituting the belt. The term "belt" should be understood to also cover the form of a mat as well as a blanket or duvet, on or in which the patient can be positioned. The blanket may envelope the legs and include, according to one embodiment, a separation of the two legs which are therefore covered separately.

Each antenna 104a, 104b is a rectangular flat antenna having an electromagnetic pole at each of its longitudinal ends.

It is advantageously made of a flexible and thin material, for example from a sheet of polymer material with a thickness of the order of 10-50 microns, preferably 30-40 microns. The thickness of the material is chosen in such a way that the energy dissipation which occurs during the operation of the antenna does not provoke an excessive elevation of its temperature, and does not bother the person.

In one embodiment, the antenna is a rectangle of polyimide on which is etched a conductive metal line, typically copper, and its main feature is that it emits, when supplied with alternating current, a magnetic field on a vector perpendicular to its surface.

The conductive line is laid out along the perimeter of the rectangle and winds over several non-contiguous turns toward the interior, so that the turns are not in contact with one another. To limit the current density in the device, the electrical conductor comprises a maximum of around ten turns in order to ensure both i) the safety of the user (limiting an excessive temperature rise that may lead to burns) and ii) an adequate magnetic field intensity. A method of etching in copper on polyimide is known to the person skilled in the art and will therefore not be described here in detail, the use of methods for etching flexible printed circuits made of polyimide being widespread in the industry.

These antennas make it possible to generate a field with a form that is similar to a horn of rectangular section.

The length of the antenna is preferably between 10 and 60 cm, also preferably between 20 and 50 cm, and also preferably between 30 and 40 cm. A dimension of the order of 35 cm in length for example makes it possible to have a flux that is relatively uniform in its growth/decay density laterally.

The width of the antenna is preferably between 1.5 and 10 cm, preferably between 2 and 6 cm. A width of the order of 3 cm notably allows for an opening conditioning the rapid decay of the power of the magnetic field as a function of the depth in the body. Beyond a depth of 3 cm, only 10% to 20% of the magnetic power remains.

The ratio between the length and the width of the antenna is preferably between 1.1:1 and 20:1. It is preferably between 5:1 and 15:1, typically of the order of 10:1. This width-by-length ratio feature makes it possible to solve the intrinsic safety issues of the device, both in electrical terms if the device were damaged, and in terms of magnetic field and of conformity of the magnetic powers in limited sections of the body, to adequate but limited depths.

Figure 3:
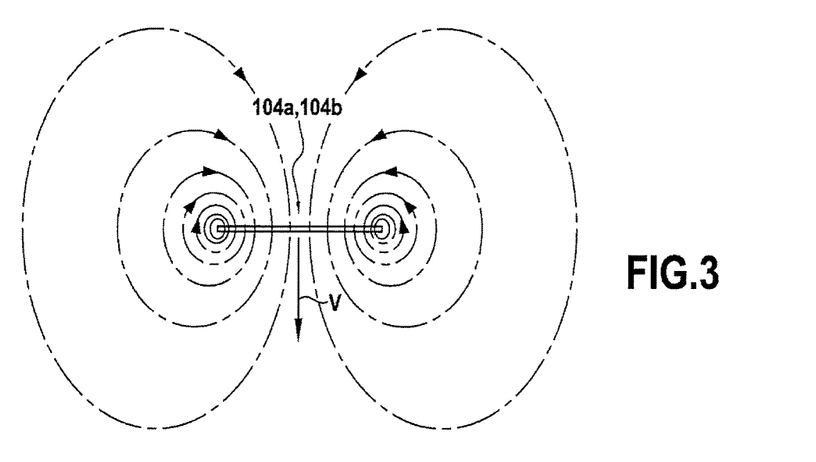
FIG. 3 is a longitudinal cross-sectional view of the magnetic field emitted by one of the antennas of the device of FIG. 2.

FIG. 3 represents, in longitudinal cross section, the form of the lines of the magnetic field emitted by each of these antennas 104a, 104b when it is supplied with alternating current. In this figure, it can clearly be seen that each longitudinal end of the antenna constitutes a pole around which field lines are formed and that the general direction of the magnetic field is given by a vector V perpendicular to the surface of the antenna. The antennas 104a, 104b of the device 100 for the abdominal belt are supplied with alternating or pulsed current by means of a power supply source 106 external to the belt.

Moreover, the antennas are electrically linked together so that the antennas of one and the same row are supplied in series. Furthermore, provision is made for the power supply to be produced in such a way that the lateral antennas 104b of one and the same row emit a magnetic field on a vector Vb opposite in direction to the vector Va on which the magnetic field emitted by the central antenna 104a is emitted (see FIG. 4).

Figure 4:
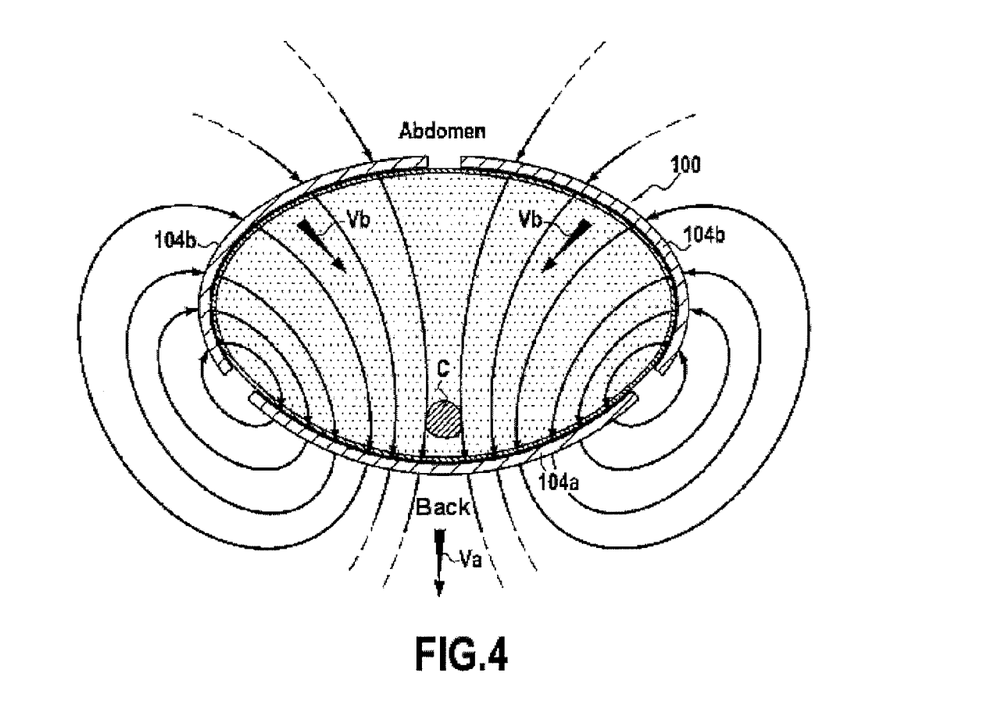
FIG. 4 is a longitudinal cross-sectional view of the magnetic field emitted by all of the antennas of the device of FIG. 2.

This means that, when the belt is closed around the abdominal belt of a person, the field lines of each row of antennas have the form represented in FIG. 4.

This figure shows (in cross section) the abdominal belt of the body of a person wearing the device 100 according to the invention, with the abdomen and the back (against which the central antennas 104a of the device are situated). It can be seen that the magnetic field lines originating from the antennas of one and the same row exhibit a maximum intensity on the skin surface to decay in depth in the body.

The magnetic field thus generated by the device therefore allows for an optimum treatment of the muscular areas situated in proximity to the hips and at the level of the abdominals (the intensity of the field being concentrated in these areas). Lying deeper, the intensity of the magnetic field being reduced, the organs of the person, and in particular the vertebral column C, are spared by the emission of the magnetic field.

Furthermore, the antennas of the device emit a magnetic field on a vector perpendicular to their surface, the magnetic field radiated below and above the abdominal belt being extremely weak. The critical organs of the person such as the heart and the lungs are therefore also spared.

To obtain such results, the alternating or pulsed power supply current for the antennas 104a, 104b of the device has a frequency of between 10 and 100 Hz, preferably between 40 and 60 Hz. It can be equal to 16 Hz, 32 Hz, 48 Hz, 64 Hz, 80 Hz or 96 Hz, preferably of the order of 50 Hz. Furthermore, when it is alternating, the power supply current advantageously has a voltage of between 5 and 25 V, preferably between 5 and 15 V. It can also be equal to 20 V in certain embodiments. The intensity of the power supply current for the device is preferably between 0.3 and 0.8 A, also preferably between 0.5 and 0.8 A, more preferentially equal to 0.5 A.

Similarly, each antenna of the device is dimensioned to emit, when it is supplied by a current exhibiting such characteristics, a magnetic field with a maximum intensity of approximately 200 µT. Once the device is applied in contact with the person, the magnetic field will be of 200 µT at its maximum on the skin surface and will not exceed 1 µT at the center of the body. It has indeed been found that the application of a magnetic field with an intensity greater than 200 µT could have, at high doses, damaging secondary effects on the cells of the brain and of the bones of the person. The limitation to such an intensity threshold of 200 µT therefore makes it possible to avoid such risks.

Figure 5:
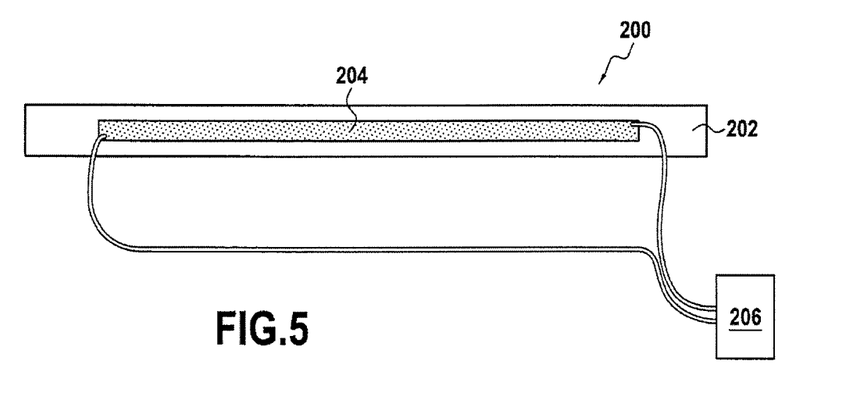
FIG. 5 is a view of the device of FIG. 1 applied to the arms of the person.

In conjunction with FIG. 5, there now follows a description of the device 200 intended to be positioned around an arm of the person.

This device 200 is identical to the one described in conjunction with the abdominal belt. In particular, it comprises a belt 202 made of insulating material, a single rectangular flat dipolar antenna 204 (identical to the one whose field lines are represented in FIG. 3), and a source 206 supplying the antenna with alternating current.

The antenna 204 extends longitudinally in the lengthwise direction of the belt 202 as represented in FIG. 5. The characteristics of the antenna and of the power supply source thereof are identical to those described in conjunction with the device for application to the abdominal belt.

Here, the belt 202 is wound helically around the arm of the person. This arrangement allows the antenna 204 to emit a magnetic field with field lines that "pass through" the arm while being canceled by those from the back of the opposite antenna segment.

This means that the intensity of the magnetic field emitted by the antenna can be adjusted according to the diameter of the arm of the person. If the patient has an arm of small diameter, the influence of the magnetic field originating from the side of the antenna which is opposite it when wound is high and in a direction opposite thereto. It thus makes it possible to partly cancel the field emitted toward the tissues of the person. On the other hand, if the patient has an arm of large diameter, the antenna of the device is positioned almost vertically in relation to this diameter. The antenna then approaches a simple vertical radiant element for which the distance between the ends becomes insignificant by virtue of the helical form of its winding.

Figure 6:
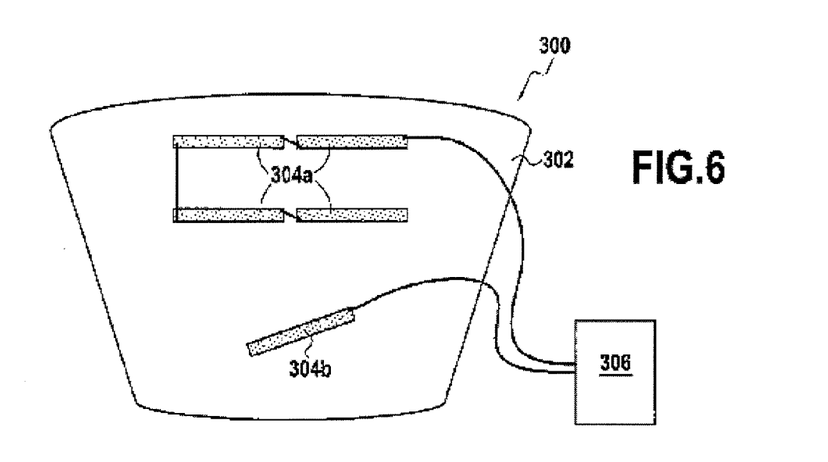
FIG. 6 is a view of the device of FIG. 1 applied to the thighs and/or to the calves of the person.

In conjunction with FIG. 6, there now follows a description of the device 300 intended to be positioned around the thigh and the calf of a leg of the person.

This device 300 is identical to the preceding ones. In particular, it comprises a belt 302 made of insulating material, five flat dipolar antennas 304a, 304b described below, and an alternating current power supply source 306 for these antennas.

The antennas are identical to those with the field lines represented in FIG. 3. They consist, on the one hand, of two parallel rows of flat dipolar antennas, each row consisting of two lateral antennas 304a supplied in series, and on the other hand of a single antenna 304b.

The antennas 304a arranged in rows extend longitudinally in the lengthwise direction of the belt 302 and are intended to surround the thigh of the person in the same way as the antennas of the device applied to the abdominal belt. As for the single antenna 304b, it also extends longitudinally in the lengthwise direction of the belt and is intended to be positioned around the corresponding calf of the person in the same way as the antenna of the device applied to the arm.

The device 300 has been described here in an application both to the thigh and to the calf of a leg of a person. It is however possible to envisage producing a separate device for each of these parts, namely a device intended to be applied to the thigh and a separate device intended to be applied to the calf.

There now follows a description of certain advantageous characteristics common to all the devices 100 to 300 described previously.

In particular, these devices preferably comprise a module for controlling the alternating current power supply source for the antenna (not represented). This control module thus makes it possible to control the intensity of the magnetic field emitted for the antenna or antennas of the device.

Moreover, again advantageously, these devices also comprise at least one magnetic field measurement sensor (not represented) positioned on the belt and linked to the control module. The presence of one or more magnetic field measurement sensors makes it possible to accurately determine the threshold of magnetic induction applied to the patient, which corresponds to the optimum intensity of the electrical current to be chosen. Based on these measurements, an adjustment can therefore be made using the control module.

In particular, the devices may comprise a means for automatically adjusting the intensity of the emitted magnetic field for the antenna or antennas based on the morphology of the users. This is done, for example, by compensating the magnetic permeability of the people that the devices can adjust. A dichotomy on the intensity of the magnetic field emitted by the antennas makes it possible to find the ideal operating point. The dichotomy converges when the magnetic field measured on the side opposite an antenna is equal, for example, to 0.01 Gauss (1 µTesla).

The invention also relates to the use of the device in esthetic treatment methods, therapeutic treatment methods, relaxation methods or methods for simulating a sporting activity.

The device of the invention is used for the emission of a magnetic field penetrating into the tissues of at least a part of at least one member and/or the trunk of a person.

A "member" should be understood in particular to mean one or both arms and one or both legs, and notably the calf or calves and the thigh or thighs, and in particular the upper part of the thigh or thighs.

The "trunk" should be understood in particular to mean the abdominal area, the lumbar region and the neck.

The weak magnetic field level required on the surface of the skin, between a tenth and a few times the earth's magnetic field (0.5 Gauss equivalent to 50 microT), makes it possible to apply these techniques without risk to the cells of the human body, or medical operation constraints.

The magnetic field applied to the living tissues makes it possible, notably by its action on the calcium channels of the cells, to simulate a sporting activity without the patient feeling any muscular contraction.

Thus, the invention relates to a method for simulating sporting activity, characterized in that it comprises the application of a magnetic field to at least a part of at least one member and/or the trunk of a person, by means of the device described previously.

The invention also relates to a muscular relaxation method or a method for improving the sleep quality, said method comprising the application of a magnetic field to at least a part of at least one member and/or the trunk of a person by means of the device described previously.

In these two methods, the device can take the form of a belt, a bracelet, a blanket or a mat.

The device of the invention very probably induces a stimulation of the calcium channels at the muscular level, that is to say at the level of the muscular fibers, under the influence of the magnetic field. The methods of the invention therefore likely comprise an activation of the energy cycle, notably by ATP hydrolysis with consequential release of energy and contraction of the muscular fibers, which provokes the lipolysis of the underlying fats, to reconstitute the ATP stock. The contraction of the muscular fibers is not felt by the person. The inventor's understanding is that the patient feels little or nothing of the muscular contractions which are stimulated chemically by action on the calcium channels because of the action of the magnetic field.

The $Ca^{2+}$-ATPases are membrane enzymes located in the membrane of the sarcoplasmic reticulum of the muscular cells where they represent 90% of the membrane proteins. The sarcoplasmic reticulum stores the $Ca^{2+}$ ions and the rapid flow of these ions from the reticulum to the sarcoplasm (cytoplasm of the muscular fibers) provokes the muscular contraction. There are two main categories of muscles:
- the striated or skeletal muscles (40% of the weight of the body, they are attached to the skeleton) for which the contraction is of electrical nature (by nerve pathway, controlled by the brain)
- the smooth muscles (10% of the weight of the body) for which the contraction, involuntary and imperceptible unlike the skeletal muscles, is of chemical nature.

This contraction linked to the $Ca^{2+}$/ATP pair is four times faster than the contraction of the striated muscles. The contraction of the smooth muscles consumes a huge amount of energy, it is the mode of operation of the main viscera such as the intestines, the blood vessels, the uterus and the kidneys. The magnetic stimulation of the $Ca^{2+}$ ions which provokes an increase in the activity of these ATPases leads de facto to a stimulation of the lipolysis of the fats stored in the smooth and striated muscles. In the case of the skeletal muscles, the ATP surplus generated by this magnetic stimulation, not accompanied by a muscular contraction, will be eliminated by the body, in the same way as a sports person does in recovery after the effort. In the context of the present invention, the electromagnetic field applied to the surface of the skin penetrates into the dermis and the body space and causes the calcium ions to resonate. The application of the electromagnetic field by the device of the invention does not provoke the destruction of the adipocytes by rupturing their membrane. On the contrary, it makes it possible to stimulate the lipolysis, that is to say the natural mechanism of the consumption of the fats contained in the adipocytes essentially situated around the viscera and the muscles.

The study carried out in the context of the invention on DNA chips has irrefutably demonstrated the genic stimulation of the calcium channels at the muscular level under the influence of the magnetic field generated by the device. By virtue of the device of the invention, there is no need to impose on the surface of the skin a magnetic field of high intensity in order to ensure an intensity at depth that is sufficient to activate the biological targets. The devices of the prior art do not make it possible to act at such a depth without compromising the safety of the person. This is because the device of the present invention allows for a targeted action of the magnetic field which radiates essentially between the two planes which are perpendicular to the surface of the antenna and which pass through its lengths. There is no diffusion of the magnetic field over an area of the body which must not be exposed to a magnetic field, such as the heart, the brain or the lungs.

According to a particular implementation, the method makes it possible to remodel the silhouette or enhance the esthetics of the body of a healthy person, i.e. a person not affected by any declared disease linked to an overload of adipose mass. Thus, one object of the invention is an esthetically-targeted non-therapeutic method for reducing the visceral or intramuscular fatty mass which comprises the application of a magnetic field to at least a part of at least one member and/or the trunk of a person by means of a device described above, in particular of a healthy person.

In this method, the device can take the form of a belt, a bracelet, a blanket or a mat. It preferably takes the form of a belt as described in FIG. 2.

The present invention also relates to a method for reducing the visceral or intramuscular fatty mass, that is to say at the level of the intramuscular adipocytes, characterized in that it comprises the application of a magnetic field to at least a part of at least one member and/or the trunk of a person. The reduction of the fatty mass at depth by the method of the present invention allows for a very effective enhancement of the attractiveness of the person, for example his or her silhouette.

The invention also relates to a method applying a magnetic field to at least a part of at least one member and/or the trunk of a person by means of the device described previously for the treatment or prevention of problems including sterility, obesity and metabolic syndrome.

A method according to the invention notably makes it possible to prevent type 2 diabetes, cardiovascular disorders and cerebrovascular accidents.

A device as described previously for its use in the treatment of sterility, obesity or metabolic syndrome also forms part of the present invention.

According to these aspects of the invention, the device can take the form of a belt, a bracelet, a blanket or a mat. It preferably takes the form of a belt as described in FIG. 2.

Thus, according to one of its aspects, the invention relates to a method that makes it possible to prevent or fight against metabolic syndrome.

Metabolic syndrome detected in a person who has not declared any particular symptom corresponds to a greater risk of metabolic disorders or illness compared to an individual said to be in good health. Metabolic syndrome can thus be defined as a risk of cardiovascular accident multiplied by three relative to an individual actually in good health. Metabolic syndrome describes a state which is considered as a precursor of a number of serious diseases including:
type 2 diabetes (DT 2);
cardiovascular disorders;
cerebrovascular accident (CVA).

The device of the invention also makes it possible to prevent or fight against obesity, in particular abdominal obesity, and consequently against the sicknesses associated with obesity. In addition, the present invention also relates to a method for treating abdominal obesity, characterized in that it comprises the application of a magnetic field to at least one part of at least one member and/or the trunk of a person by means of the device described previously.

The devices of the prior art do not make it possible to stimulate lipolysis at depth in the tissues. A surprising discovery is that the magnetic field generated by the device of the invention, in particular according to the variants and refinements of the present invention, provokes the consumption of the fat situated at depth, notably under the dermis, in the viscera or the muscles.

The magnetic field generated by the antenna on the surface of the skin penetrates into the body to a given depth, typically of the order of 2 to 10 cm, preferably to more than 5 cm, over the entire surface of the antenna. Its intensity decreases with the depth.

Finally, it has been discovered, unexpectedly, that a magnetic field exhibiting the intensity and the frequency mentioned above also has an activity for stimulating and/or improving oogenesis and spermatogenesis. Thus, the present invention also covers a method for provoking or increasing oogenesis and/or spermatogenesis in a person or an animal, in particular a mammal, having need thereof. The method of the invention makes it possible to treat sterility, increase fertility, and prevent a risk of sterility, particularly when it evolves from an obesity or a high obesity risk which must be fought against. The method of the invention can be applied to women and to men.

In the context of this method, any device known to the person skilled in the art for emitting a magnetic field with an intensity and frequency conforming to those described above can be used. The device according to the invention will preferably be chosen for the additional advantages procured by them.

Fertility is dependent on the presence in the body of gametes (ovocytes or spermatozoons) and sterility can have various causes, including problems in the production of gametes. In a woman in particular, sterility can evolve from ovulation problems (the polycystic ovaries or the endometriosis which disrupts ovulation or the nidation of the embryo), obstruction or alteration of the tubes, or from a cervical mucous anomaly. Within the meaning of the present invention, the expression "treatment or prevention of sterility" should be understood to mean the treatment or the prevention of the problems that have just been described, in particular the stimulation or increase of oogenesis or of spermatogenesis, particularly in the case where the latter is non-existent or when it is inadequate. In one implementation of the invention, the treatment of sterility leads to the increase in the pregnancy rate among people following a medically-assisted procreation protocol, by differing techniques, for example by conventional in-vitro fertilization (IVF), by in-vitro fertilization with microinjection (ICSI: intra-cytoplasmic sperm injection), by microinjection with chosen spermatozoons (IMSI: morphologically selected sperm injection or SICSI: scored intra-cytoplasmic sperm injection).

One object of the invention is thus a method applying a magnetic field likely to be generated by the device described above to improve fertility, in particular among people suffering from obesity, in particular in women or men who have a body mass index (BMI) greater than or equal to 30. It has been demonstrated, by a study conducted in a hospital environment, that obese patients—patients judged to be sterile following functional exploration examinations and biological balances (FSH/LH dosage, ovarian reserve, ovocyte quality, spermogram)—can, totally unexpectedly, improve their chances of having a child through medically-assisted procreation channels. In this method, the device can take any possible form, preferably that of an abdominal belt. The duration of the sessions of exposure to the magnetic field is generally between 15 and 75 minutes. Depending on the desired result it can be 30 or 60 minutes.

In all the methods that have just been described, the parameters of dimension and form of the antenna, of intensity and of voltage of the electrical current supplying the antenna, of duration of the sessions of exposure to the magnetic field, of the number of sessions depending on the desired result, are adapted.

Advantageously, the magnetic field, when generated by an alternating current, has a frequency of between 10 and 100 hertz, for example equal to 16 Hz, 32 Hz, 48 Hz, 50 Hz, 64 Hz, 80 Hz or 96 Hz, and an intensity of between 1 and 400 microT (0.01 and 4 Gauss), and preferably between 10 and 200 microT (0.1 and 2 Gauss). The intensity of the electromagnetic field generated on the surface of the skin will preferably be limited to 200 microTesla (2 Gauss).

According to one advantageous embodiment, the method comprises a control of a dosage of a magnetic field applied to the patient. This constitutes, in particular, a significant improvement on the known devices described in the patents cited previously.

This control of the dosage is in particular performed by regulating the intensity of the magnetic field. This control of the dosage can easily be done by varying the intensity of the electrical current supplying the antenna and generating the magnetic field, which is typically between 0.3 and 0.8 A.

According to one of its aspects, the invention also relates to a method for controlling the dosage of a magnetic field applied to a person, particularly for an esthetic or therapeutic treatment purpose, characterized in that it comprises the positioning of a magnetic wave sensor in immediate proximity to a radiating antenna, said magnetic wave sensor being in communication with a magnetic field control module, said control module communicating with one or more radiating antennas, and the measurement by the control module of the magnetic permeability of the person in order to adapt the magnetic field emitted by the radiating antenna or antennas according to an individual profile, notably by reducing or increasing the intensity of the current.

This notably allows for a dosage in terms of intensity and of duration of the magnetic field applied to the person.

The invention also relates, according to another aspect, to a method for measuring the response of the tissues of a person to contact with a magnetic field, notably in order to optimize an esthetic or therapeutic treatment by magnetic field, characterized in that said method comprises varying the frequencies of the electromagnetic field, preferably between 10 Hz and 10 kHz, with respect to one or more parts of one or more members and/or one or more parts of the trunk of a person, and the measurement of the electromagnetic field to estimate the response of the tissues of the person. The electrical field component, present throughout the electromagnetic field, becomes significant from 1 KHz, whereas, at 50 Hz, the electromagnetic field is primarily characterized by a predominant magnetic field. This electrical field then makes it possible to perform a fine measurement of the magnetic permeability.

This method notably makes it possible to estimate the fatty mass and/or the muscular mass in order in particular to adapt the intensity and the duration of the magnetic field applied to the person.

This method can, for example, be implemented by passing an alternating current through all the antennas, then successively or simultaneously switching off one or more antennas to measure the electromagnetic field emitted by the remaining antennas. Thus, by measuring the electromagnetic field emitted through the tissues of a person, for example by positioning the electromagnetic sensor diametrically opposite the antenna emitting the field to be measured, the electromagnetic field picked up models the magnetic permeability of the person. For the abdominal part, it is easily possible to allow only the dorsal antenna 104a to emit and measure the field which is received in the abdominal part. The belt of the device may therefore comprise an electromagnetic sensor positioned diametrically opposite at least one antenna when the belt is placed in position on the patient. The electromagnetic sensor can be one of the opposite antennas, but used in received mode to detect the signal level passing through the patient.

It is then possible to distinguish dielectric permittivity ratios of several orders of magnitude between 10 Hz and 10 KHz, which can actually be measured between 1 KHz and 10

KHz. It is possible to produce a curve of variation of dielectric permittivity of the fat (measured on the breast for example) as a function of frequency and another curve of variation of dielectric permittivity of the muscular tissue as a function of frequency. The presence of a fat-type curve slope rather than a muscle-type curve slope makes it possible to evaluate the ratios of tissues to be treated. This information is complemented by the knowledge of the weight and size of the person.

According to a particular embodiment, the method of the invention comprises the estimation of the response of the tissues of the person by varying the frequencies of the magnetic field on one or more parts of one or more members and/or parts of the trunk of the person. For example, the measurement is performed via a magnetic sensor, and for example a Hall effect or magnetoresistive sensor, notably to determine the maximum and/or optimum power threshold of the magnetic field to be applied to the person.

To implement the method of the invention, it is preferable to emit an alternating magnetic field targeted on certain areas of the body, and notably situated in the areas of high muscle and/or viscera density. The action of the magnetic field consists in interacting with certain elements involved in the cycles of consumption of the energies stored in the body (fats). In particular, the organic cycles linked to calcium are overactivated (ATPases, $Ca^{2+}$).

The effect of the magnetic field was measured by performing a dosing of certain blood components before and after a course of 12 sessions. A DNA chip analysis made it possible to validate the biochemical chain activated by the device. It also made it possible to plot a calibration curve of the intensity of the magnetic field applied as a function of the morphology of the person, for example of his or her waist size, the diameter of his or her arms or of his or her legs.

EXAMPLES

Example 1

Production of an Expression Profile

The aim of the study was to produce an expression profile to characterize the transcriptional effects induced on blood cells of people subjected to a low-frequency alternating magnetic field.

The study of the gene networks was performed by an analytical search engine.

The total RNAs extracted from cells are treated in order to obtain fluorescent molecules. These molecules are then deposited on microarrays and react with the DNA sequences of the different corresponding genes, on the basis of their complementarity. Then, the fluorescence is measured using a specific scanner and the quantity of RNA produced in the cell can thus be quantified inasmuch as the measured intensity is proportional to the quantity of RNA which interacts with the deposited DNA sequences. These methods are known to the person skilled in the art.

Study protocol:
11 overweight people are selected for the study. The volunteers, 4 men and 7 women, had an age of between 38 and 64 years and, for ten of them, had an established excess weight.
a first blood sampling was performed for all of the 11 people (biological balance prescribed by an endocrinologist) before the start of the study.
a second blood sample was performed after the 12 sessions.

Out of the people in the study, 4 people (2 men, 2 women) additionally performed a sampling at the start and at the end of the 8 th session.

The sessions consisted in positioning the lower part of the body of the person (up to the thorax) in a blanket enclosing the antennas of the device of the present invention. The blanket had a separation for the legs. Three antennas were provided for the abdominal part, two for each thigh, one for each calf, and one for each arm. The antenna for the calves and the arms was positioned helically around the member. The blanket was linked to the control module generating the magnetic field.

The electrical current supplying the device conformed to the following values: the frequency used was 50 Hz, the voltage 20 V and the intensity between 500 and 800 mA.

Each session lasted approximately 60 minutes.

The results were obtained from a selection of genes that met the following criteria:

(1) The activations (induction greater than ×1.50 compared to the expression control which is the expression of the gene before the study) were observed at least in 3 people out of 4, in an analysis limited to the people who had performed the 4 samplings.

(2) It was found that the activation of these genes for these people was maintained during the different sessions.

(3) The genes retained were conserved only if their modulation was found at least for 6 subjects out of 11.

(4) To be part of a biological functional network in which a number of genes exhibiting a significant modulation are associated. This study was performed on the basis of the study of the expression profile on agilent whole genome microarray chips, comprising 43 776 genetic sequences (excluding controls).

These chips were hybridized with probes corresponding to the RNA samples extracted from whole blood. The quality and the quantity of all of the samples of the RNAs were measured.

A control biological balance was produced for all of the patients.

Analysis of the results:

The data was subjected to an intra-chip and inter-chip normalization (quantile method) using specific software.

The ratios of the intensities: after the sessions versus before the first session were calculated for each person in order to give the induction or the inhibition (modulation) of each gene to study for each person.

A gene selection was performed to select genes in which the expression ratio shows a modulation at least in three of the four people having benefitted from an analysis before and after the 8th session.

Only the genes which exhibited a modulation in the conditions: before/after the 8th session and after the 12th session were considered.

This analysis resulted in the selection of 112 genes which were subjected to a correlation study.

In a second stage, the intensity data obtained after normalization were filtered on the basis of an intensity greater than the background noise for all the samples, and an intensity ratio greater than 1.5.

This selection identified 89 genes.

The relevance of the results obtained resulted in the analysis being continued on the other 7 people. Out of these 7 people, 3 showed similar inductions for the 112 genes selected (a fourth does however retain a significant modulation).

Of the remaining people, the gene expression of one person remains stable whereas two have inverted expression ratios.

It was observed that the induction ratios remain overall induced in time (day 8-1, day 8-2, day 12 versus day 0) at least in the three people out of four sampled.

Conclusion:

Overall, the analysis of these two selections revealed functions associated primarily with the muscle and with calcium regulation.

Ultimately, this study led to the following classification according to the modulation of the expression in response to the effects of the device of the generator of a low-frequency alternating magnetic field.

A strong response was found for 6 people, a significant response for 2 people, and no response for 3 people.

The magnetic fields generated by the device of the invention induce muscular contractions similar to those resulting from a sustained physical exercise, which is associated with the induction of a set of the genes identified in this study.

Furthermore, the induced muscular contraction increases the activity of the lipase (HSL) which, after translocation of the cytosol to the lipid droplets, promotes hydrolysis of the intramuscular triglycerides.

Thus, these observations tend to demonstrate that the action of the appliance on the muscular contraction is accompanied by a redistribution of the cholesterol at the cellular level, regulating the functions of the calcium channels and the membrane potential.

Thus, the device of the present invention has a positive action on the lipids accumulated abnormally around the viscera or in the muscles, particularly at the waist size level, which means that it has a positive role to play in the prevention of risks associated with metabolic syndrome.

The device of the present invention acts in parallel on the removal of the lipids contained naturally in the hypodermis, which contributes to also using this appliance for bodily esthetic remodeling.

Example 2

Study on the Waist Size of People

At the same time, the capacity of the device of the invention to induce a reduction in the waist size was assessed, after 12 60-minute sessions, in 11 overweight or obese people (severe obesity or morbidity excluded), not involved in a slimming program.

This study was performed on the 11 people of example 1. At the end, the waist size of the volunteers had reduced by more than 6.0 cm on average after the 12 sessions.

These results therefore confirm the results of the gene expression study of example 1, and the different metabolic pathways identified as being modulated by the device of the invention.

Example 3

Study Relating to the Evaluation of the Fertility Parameters of Overweight Sterile Patients After A Reduction of Their Waist Size by Application of the Method of the Invention The study was conducted at the medically-assisted procreation center of the department of reproduction medicine at the Antoine Béclère hospital which, in September 2010, became the referral center for in vitro fertilization (IVF) for obese people in France.

Its aim was to evaluate the effect of a method according to the invention accompanied by a balanced, non-slimming diet, on the results of inclusion in medically-assisted procreation by IVF for sterile patients exhibiting abdominal obesity.

The sterility of the patient is diagnosed by the treating gynecologist after functional exploration and production of husband-wife biological balances (FSH/LH dosage—ovarian reserve—ovocyte quality—spermogram).

The study related to two groups of obese patients, comparison group A and group B.

Each patient from group A followed the following protocol:

first visit to perform a balance on the ovarian reserve. Pelvic echograph and blood dosing carried out. Nutritional advice.

second visit 6 weeks after the first to repeat a check on the ovarian presence.

ovarian stimulation with follow-up by echography and blood dosings to evaluate the ovarian response.

ovarian puncture to evaluate the number of ovocytes obtained.

in-vitro fertilization.

Group A was made up of a 109 patients.

Group B included 17 obese patients, 7 with class 1 obesity (corresponding to a BMI of between 30 and 34.9), 5 with class 2 obesity (corresponding to a BMI or between 35 to 39.9) and 5 with class 3 obesity (corresponding to a BMI of 40 or above). BMI stands for body mass index. A patient is considered obese when his or her BMI is greater than or equal to 30.

The protocol followed by the patients from group B corresponded to that of the patients from group A; the patients from group B additionally followed two treatment sessions according to the invention, over 6 weeks, between the first and the second visit. The weight and the waist size of the patients from this group were measured in the first session, in the sixth session and in the twelfth session.

The treatment for the patients consisted in 12 sessions distributed over 6 weeks with 2 sessions per week, each session being managed by a nurse. The duration of the sessions was 30 minutes using the abdominal belt described previously, notably in FIG. 2. The intensity of the current was 0.5 A, the frequency of the current was 50 Hz and the voltage was 9.9 volts.

The in-vitro fertilization protocol followed was conventional and was the same for both groups. A detailed description of it can be obtained from the hospital establishment.

The preliminary results showed an improvement in the average pregnancy rate among the obese patients from group B who had followed the method according to the invention (equal to 41.18%) compared to the average pregnancy rate among the obese patients from the reference group A who had not followed the treatment (27%). Out of the 7 pregnancies in group B, there were two spontaneous pregnancies.

The average waist size of group B reduced by 5.4 cm on completion of the 12 sessions.

29.41% of the patients from group B were class 3 compared to only 2.75% of the patients from group A.

The difference in the number of class 3 patients between the two groups is linked to the fact that many patients from group A who was in class 3 initially followed a slimming diet to begin the protocol at the time when it changed to class 2, even directly to class 1.

The results are given in the table below.

| Classification | BMI | Comparison group A | | | Group B | | |
| --- | --- | --- | --- | --- | --- | --- | --- |
| | | Number of patients | Number of pregnancies | Pregnancy rate | Number of patients | Number of pregnancies | Pregnancy rate |
| Class 1 obesity | 30 to 34.9 | 77 | 23 | 29.87% | 7 | 1 | 14.29% |
| Class 2 obesity | 35 to 39.9 | 29 | 7 | 24.14% | 5 | 4 | 80.00% |
| Class 3 obesity (morbid obesity) | 40 or more | 3 | 0 | 0% | 5 | 2 | 40.00% |
| Total number | | 109 | 30 | 27.00% | 17 | 7 | 41.18% |

On completion of this study, there was a demonstrable reduction in the waist size as well as a significant improvement in the pregnancy rate among obese patients, regardless of their BMI value, using the method of the present invention.

The invention claimed is:

1. A device for exposing at least one part of a person's body to a magnetic field, comprising:
    an insulating belt applied on the at least one part of a person's body; and
    at least one substantially rectangular flat dipolar antenna emitting a magnetic field on a vector perpendicular to its surface, the antenna having a selected width-by-length ratio between 5:1 and 20:1 for providing: a flux that is uniform in its growth and decay density laterally and a decay rate of the magnetic field as a function of a penetration depth of the magnetic field in the at least one part of the person's body;
    wherein the antenna is positioned longitudinally on the belt in the lengthwise direction thereof.

2. The device of claim 1, further comprising an alternating or pulsed current power supply source for the antenna to generate a current having a frequency of between 10 and 100 Hz.

3. The device of claim 2, wherein the alternating or pulsed current power supply source for the antenna generates a current having a frequency of between 40 and 60 Hz.

4. The device of claim 2, wherein the alternating or pulsed current power supply source has a voltage of between 5 and 25 V and an intensity of between 0.3 and 0.8 A.

5. The device of claim 1, wherein the antenna is dimensioned to emit the magnetic field with a maximum intensity between 1 and 400 µT.

6. The device of claim 1, wherein the belt is an abdominal belt having two parallel rows of flat dipolar antennas, each row consisting of a central antenna positioned between two lateral antennas, the antennas of one and the same row being supplied in series.

7. The device of claim 6, wherein the antennas of one and the same row are supplied with an alternating current in such a way that the central antenna emits the magnetic field on a vector opposite in direction to the vector on which the magnetic field emitted by the lateral antennas is emitted.

8. The device of claim 1, wherein the belt has a single flat dipolar antenna, and wherein the device can be placed around the person's aim or calf.

9. The device of claim 1, wherein the belt has two parallel rows of flat dipolar antennas, each row consisting of two lateral antennas supplied in series, and wherein the device can be placed around the person's thigh.

10. The device of claim 1, further comprising a mat comprising at least two flat dipolar antennas positioned parallel in their lengthwise direction.

11. The device of claim 1, further comprising a mat comprising at least four flat dipolar antennas positioned parallel in their lengthwise direction.

12. The device of claim 1, further comprising a module for controlling the alternating or pulsed current power supply source for the antenna, and at least one magnetic field measurement sensor positioned on the belt and linked to said module.

13. A method for reducing visceral or intramuscular fatty mass in a person in need thereof, the method comprising:
    applying an insulating belt of a device on at least one part of a person's body;
    configuring at least one substantially rectangular flat dipolar antenna of the device to emit a magnetic field on a vector perpendicular to its surface, the antenna having a selected width-by-length ratio between 5:1 and 20:1 for providing: a flux that is uniform in its growth and decay density laterally and a decay rate of the magnetic field as a function of a penetration depth of the magnetic field in the at least one part of the person's body; and
    wherein the antenna is positioned longitudinally on the belt in the lengthwise direction thereof.

14. The method of claim 13, wherein the person is an obese person.

15. The method of claim 13, wherein the device is positioned around the person's waist.

16. The method of claim 13, wherein the method increases fertility in a person in need thereof.

17. The method of claim 13, wherein the method reduces waist size in a person in need thereof.

18. The method of claim 13, further comprising:
    exposing the at least one part of the person's body to the emitted magnetic field.

19. The method of claim 18, further comprising:
    controlling an intensity of the emitted magnetic field with a magnetic wave sensor placed in immediate proximity of the device, and linked to a magnetic field control module that measures the person's magnetic permeability.

20. The method of claim 18, further comprising, prior to the exposing:
    estimating a fatty mass and/or a muscular mass of the at least one part of the person's body in order to choose an intensity of the emitted magnetic field and/or the length of time for exposing the at least one part of the person's body with the emitted magnetic field during the exposing.

21. The method of claim 20, wherein the estimating is performed with a Hall or magnetoresistive sensor that determines the maximum and/or optimum power threshold of the emitted magnetic field.

22. The device of claim 1, wherein the selected width-by-length ratio is between 10:1 and 15:1.

23. The device of claim 1, wherein the antenna has a length between 10 and 60 cm, or between 20 and 50 cm, or between 30 and 40 cm.

24. The device of claim 23, wherein the antenna is configured to have the length to make the flux uniform in its growth and decay density laterally.

25. The device of claim 1, wherein the antenna has a width between 1.5 and 10 cm, or between 2 and 6 cm.

26. The device of claim 25, wherein the antenna is configured to have the width to allow for a rapid decay of power of the magnetic field as a function of a depth in the body such that only 10% to 20% of the magnetic power remains beyond a depth of 3 cm.

27. The method of claim 13, wherein the selected width-by-length ratio between 10:1 and 15:1.

28. The method of claim 13, wherein the antenna has a length between 10 and 60 cm, or between 20 and 50 cm, or between 30 and 40 cm.

29. The method of claim 28, wherein the antenna is configured to have the length to make the flux uniform in its growth and decay density laterally.

30. The method of claim 13, wherein the antenna has a width between 1.5 and 10 cm, or between 2 and 6 cm.

31. The method of claim 30, wherein the antenna is configured to have the width to allow for a rapid decay of power of the magnetic field as a function of a depth in the body such that only 10% to 20% of the magnetic power remains beyond a depth of 3 cm.

32. A method for reducing visceral or intramuscular fatty mass, the method using a device comprising an insulating belt having two parallel rows of rectangular flat dipolar antennas, each row consisting of at least three antennas in series: a central antenna positioned between two lateral antennas positioned in their lengthwise direction, and a power supply source for the antennas, the method comprising:
configuring the rectangular flat dipolar antennas of the device to emit a magnetic field on a vector perpendicular to the belt surface, the antennas having a selected width-by-length ratio for providing: a flux that is uniform in its growth and decay density laterally and a decay rate of the magnetic field as a function of a penetration depth of the magnetic field in the at least one part of the person's body;
applying the device on at least one part of a person's body comprising visceral or intramuscular fatty mass;
supplying the antennas of one and the same row with an alternating or pulsed current power supply source such that the central antenna emits a magnetic field on a vector opposite in direction to the vector on which a magnetic field emitted by the lateral antennas is emitted, so that organs of the person, and in particular the vertebral column are spared by an emission of the magnetic field, and the antennas emit a magnetic field in visceral or intramuscular fatty mass that has a frequency of between 10 and 100 hertz, and an intensity of between 1 and 400 microT (0.01 and 4 Gauss); and
exposing the visceral or intramuscular fatty mass of the at least one part of the person's body waist to the magnetic field that is emitted by the antennas for a time sufficient to reduce said fatty mass.

33. The method of claim 32, wherein the antennas are configured to have a width-by-length ratio between 5:1 and 20:1.

34. The method of claim 32, wherein the antennas are configured to have a width-by-length ratio between 10:1 and 15:1.

35. The method of claim 32, wherein the antennas are configured to have a length between 10 and 60 cm, or between 20 and 50 cm, or between 30 and 40 cm.

36. The method of claim 35, wherein the antennas are configured to have the length to make the flux uniform in its growth and decay density laterally.

37. The method of claim 32, wherein the antennas are configured to have a width between 1.5 and 10 cm, or between 2 and 6 cm.

38. The method of claim 37, wherein the antennas are configured to have the width to allow for a rapid decay of power of the magnetic field as a function of a depth in the body such that only 10% to 20% of the magnetic power remains beyond a depth of 3 cm.

39. The method of claim 32, wherein the person is an obese person.

40. The method of claim 32, wherein the method increases fertility in an obese person in need thereof.

41. The method of claim 32, wherein the method reduces waist size in a person in need thereof.

42. The method of claim 32, further comprising:
controlling an intensity of the emitted magnetic field with a magnetic wave sensor placed in immediate proximity of the device, and linked to a magnetic field control module that measures the person's magnetic permeability.

43. The method of claim 32, further comprising, prior to the exposing:
estimating a fatty mass and/or of the muscular mass of the at least one part of the person's body in order to choose an intensity of the emitted magnetic field and/or the length of time for exposing the at least one part of the person's body with the emitted magnetic field during the exposing.

44. The method of claim 43, wherein the estimating is performed with a Hall or magnetoresistive sensor that determines the maximum and/or optimum power threshold of the emitted magnetic field.

45. A method for reducing visceral or intramuscular fatty mass, the method using a device comprising an insulating belt having at least two parallel rows of flat dipolar antennas, each row consisting of at least three antennas in series: a central antenna positioned between two lateral antennas positioned in their lengthwise direction, and a power supply source for the antennas, the method comprising:
configuring the flat dipolar antennas of the device to emit a magnetic field on a vector perpendicular to the belt surface, the antennas having a selected length and a selected width, for providing a flux that is uniform in its growth and decay density laterally and a decay rate of the magnetic field as a function of a penetration depth of the magnetic field in the at least one part of the person's body;
applying the device on at least one part of a person's body comprising visceral or intramuscular fatty mass;
supplying the antennas of one and the same row with an alternating or pulsed current power supply source, so that organs of the person are spared by an emission of the magnetic field, and the antennas emit a magnetic field in visceral or intramuscular fatty mass that has a frequency of between 10 and 100 hertz, and an intensity of between 1 and 400 microT (0.01 and 4 Gauss); and
exposing the visceral or intramuscular fatty mass of the at least one part of the person's body to the magnetic field that is emitted by the antennas, for a time sufficient to reduce said fatty mass.

\* \* \* \* \*